US010683481B2

(12) United States Patent
Yu et al.

(10) Patent No.: US 10,683,481 B2
(45) Date of Patent: Jun. 16, 2020

(54) ULTRAHIGH-PRESSURE HOMOGENIZING INTEGRATED DEVICE AND CELL DISRUPTOR

(71) Applicant: Guangzhou Juneng Nano&Bio Technology Co., Ltd, Guangzhou, Guangdong Province (CN)

(72) Inventors: XingWen Yu, Guangzhou (CN); Qian Yu, Guangzhou (CN)

(73) Assignee: Guangzhou Juneng Nano & Bio Technology Co., Ltd, Guangzhou (CN)

(*) Notice: Subject to any disclaimer, the term of this patent is extended or adjusted under 35 U.S.C. 154(b) by 659 days.

(21) Appl. No.: 15/319,378

(22) PCT Filed: Mar. 31, 2015

(86) PCT No.: PCT/CN2015/075445
§ 371 (c)(1),
(2) Date: Dec. 16, 2016

(87) PCT Pub. No.: WO2016/037482
PCT Pub. Date: Mar. 17, 2016

(65) Prior Publication Data
US 2017/0145376 A1 May 25, 2017

(30) Foreign Application Priority Data
Sep. 11, 2014 (CN) .......................... 2014 1 0461556
Sep. 11, 2014 (CN) .......................... 2014 1 0461557

(51) Int. Cl.
*C12M 1/00* (2006.01)
*C12M 1/33* (2006.01)
(Continued)

(52) U.S. Cl.
CPC ............ *C12M 47/06* (2013.01); *C12M 23/34* (2013.01); *C12M 27/00* (2013.01); *C12M 29/14* (2013.01);
(Continued)

(58) Field of Classification Search
CPC ...... C12M 47/06; C12M 47/08; C12M 23/34; C12M 33/12; C12M 41/40; C12M 29/00; F04B 9/113; B01F 5/02
(Continued)

(56) References Cited

U.S. PATENT DOCUMENTS 3,887,144 A * 6/1975 Schaeffer ............ B02C 19/0056
241/301
7,240,862 B2 * 7/2007 Grasselli ............... B01F 5/0663
241/2

FOREIGN PATENT DOCUMENTS

CN 201175652 Y * 1/2009
CN 101624566 1/2010
(Continued)

OTHER PUBLICATIONS

"International Search Report (Form PCT/ISA/210) of PCT/CN/2015/075445", dated Jun. 9, 2015, with English translation thereof, pp. 1-4.

*Primary Examiner* — Kenneth E Peterson
*Assistant Examiner* — Nhat Chieu Q Do
(74) *Attorney, Agent, or Firm* — JCIPRNET

(57) ABSTRACT

Disclosed is an ultrahigh-pressure homogenizing integrated device and a cell disruptor. The ultrahigh-pressure homogenizing integrated device includes a long oil cylinder, a main connecting sleeve, a high-pressure cylinder homogenizing main body, an auxiliary connecting sleeve and a short oil cylinder, which are sequentially and coaxially arranged. An upper part of the high-pressure cylinder homogenizing main
(Continued)

body is provided with a feeding hole communicated with a high-pressure cavity; and the feeding hole is connected with an integrated feeding device. A pressurizing plunger rod in the high-pressure cavity of the high-pressure cylinder homogenizing main body is connected with a piston rod of the long oil cylinder; and a homogenizing valve arranged in the inner cavity, which is communicated with the high-pressure cavity, of the high-pressure cylinder homogenizing main body, is connected with an ejector rod of the short oil cylinder.

10 Claims, 4 Drawing Sheets

(51) Int. Cl.
*C12M 1/02* (2006.01)
*F04B 31/00* (2006.01)
*F04B 9/113* (2006.01)
*C12M 1/26* (2006.01)
*C12M 1/34* (2006.01)

(52) U.S. Cl.
CPC ............ *C12M 33/12* (2013.01); *C12M 41/40* (2013.01); *C12M 45/02* (2013.01); *C12M 47/08* (2013.01); *F04B 9/113* (2013.01); *F04B 31/00* (2013.01)

(58) Field of Classification Search
USPC .......................................... 241/83; 435/306.1
See application file for complete search history.

(56) References Cited

FOREIGN PATENT DOCUMENTS

| CN | 201381310 Y | * | 1/2010 | ............ C12M 47/06 |
|---|---|---|---|---|
| CN | 104195039 | | 12/2014 | |
| CN | 104212710 | | 12/2014 | |
| CN | 204079977 | | 1/2015 | |
| CN | 204079979 | | 1/2015 | |

* cited by examiner

ULTRAHIGH-PRESSURE HOMOGENIZING INTEGRATED DEVICE AND CELL DISRUPTOR

CROSS-REFERENCE TO RELATED APPLICATION

This application is a 371 application of an international PCT application serial no. PCT/CN2015/075445, filed on Mar. 31, 2015, which claims priority to and the benefit of China Patent Application No. CN201410461556.0 and CN201410461557.5, filed on Sep. 11, 2014, the disclosure of which is incorporated herein by reference in its entirety.

BACKGROUND OF THE INVENTION

1. Field of the Invention

The present invention generally relates to an ultrahigh-pressure cell disruption device, in particular, to an ultrahigh-pressure homogenizing integrated device and a cell disruptor.

2. Description of Related Art

Cell disruption is referred to a technology of disrupting cell membranes and cell walls via an external force, so that a cell content including a target component is released. The technology is fundamental to purification of a non-secretion type biochemical material (product) synthesized in cells. Combining great improvements of DNA recombination technology and tissue culture technology, proteins used to be considered as being difficult to obtain can be massively produced nowadays. Various methods for cell disruption have been developed for cell wall disruption of different purposes and types. Disruption methods can be divided into two major categories of mechanical methods and non-mechanical methods. Various equipments are applied in the mechanical methods, wherein an ultrahigh-pressure cell disruption device is generally used in disruption, microdispersion, particle nanonization and emulsification processing of biological cells, medicines, food, milk, cosmetics, chemical engineering materials, nano-materials and so forth. Disadvantages of the ultrahigh-pressure cell disruption device include: point (1): applying a crank mechanism for driving, such that the ultrahigh-pressure cell disruption device cannot be turned off or turned on, operated without loading, and immersed in circulated water bath, is operated at quick increase of temperature, cannot be operated for a long time under a high pressure state, and is susceptible to leakage due to large amount of joints; point (2): a liquid outlet is disposed at a upper part of a pressurizing homogenized device, which causes difficulty in discharging liquid, i.e., residuals are easily formed; point (3): a pressure gauge of the pressurizing homogenized device is directly connected with a high-pressure cavity, which results in frequent pulsation of the pressure gauge that causes failure; point (4): releasing energy at high pressure is likely to raise temperature; point (5): a high-pressure homogenized valve is susceptible to wear. Thus, a novel ultrahigh-pressure cell disruption device is necessary to be developed to address the afore-mentioned issues.

SUMMARY OF THE INVENTION

A first object of the present invention is to provide an ultrahigh-pressure homogenizing integrated device having a compact structure, improved operation stability and a reduced occupied space, which is advantageous for miniaturization.

A second object of the present invention is to provide a cell disruptor which has a compact structure, reduced volume and reduced occupied space, can be turned off/on and operated without loading under a state of high pressure, is operated at consistent temperature, and has fewer connection pipes and joints to prevent occurrence of leakage.

According to the afore-mentioned first object, an ultrahigh-pressure homogenizing integrated device is provided by the present invention. The ultrahigh-pressure homogenizing integrated device includes a long oil cylinder, a main connecting sleeve, a high-pressure cylinder homogenizing main body, an auxiliary connecting sleeve and a short oil cylinder, wherein a feeding hole communicated with a high-pressure cavity is disposed at an upper part of the high-pressure cylinder homogenizing main body, an integrated feeding device is connected with the feeding hole, the long oil cylinder, the main connecting sleeve, the high-pressure cylinder homogenizing main body, the auxiliary connecting sleeve and the short oil cylinder are sequentially and coaxially arranged, and a pressurizing plunger rod in the high-pressure cavity of the high-pressure cylinder homogenizing main body is connected with a piston rod of the long oil cylinder, a homogenizing valve in an inner cavity, which is communicated with the high-pressure cavity, of the high-pressure cylinder homogenizing main body is connected with an ejector rod of the short oil cylinder.

The long oil cylinder, the main connecting sleeve, the high-pressure cylinder homogenizing main body, the auxiliary connecting sleeve and the short oil cylinder of the present invention are sequentially and coaxially arranged. Thus, the ultrahigh-pressure homogenizing integrated device can be operated with less vibration and great stability, and has a compact structure and small occupied space that is advantageous for miniaturization.

As a further improvement of the present invention, a pressure gauge connection port is disposed at a left side of the high-pressure cylinder homogenizing main body and communicated with the high-pressure cavity, a first check valve is disposed in the pressure gauge connection port, a portion of a valve body of the first check valve is in the high-pressure cylinder homogenizing main body, and composes an integrated structure with the high-pressure cylinder homogenizing main body, a liquid outlet communicated with a sample outlet cavity of the high-pressure cylinder homogenizing main body is further disposed at the high-pressure cylinder homogenizing main body, the liquid outlet is located at a right side of the high-pressure cylinder homogenizing main body and communicated with a bottom part of the sample outlet cavity, and an angle between an axial line of the liquid outlet and a horizontal direction is 20°. Comparing to the check valve in the prior art, a portion of the valve body of the first check valve of the present invention is located in the high-pressure cylinder homogenizing main body and composes an integrated structure with the high-pressure cylinder homogenizing main body. As a result, the structure of the ultrahigh-pressure homogenizing main body in the present invention is more compact, so as to be advantageous for miniaturization design, and can prevent from pulsations of a high-pressure gauge that avoids the high-pressure gauge from damaging. Comparing to a liquid outlet disposed at a top part of the high-pressure cylinder homogenizing main body in the prior art, the liquid outlet in the present invention is located at a right side of the high-pressure cylinder homogenizing main body and connected with a bottom part of the sample outlet cavity, and the angle between the axial line of the liquid outlet and the horizontal direction is 20°, a resistance of liquid discharging of the liquid outlet of the present invention is reduced, so that liquid discharge is more fluent, and is not susceptible to leaving residuals. In addition, it is very convenient to arrange a liquid outlet pipe on the liquid outlet, and a length of the liquid outlet pipe connected with the liquid outlet can be reduced, so as to reduce an occupied space.

As a further improvement of the present invention, the sample outlet cavity is in a ring shape, and the axial line of the liquid outlet is tangent to a circumference of the bottom part of the sample outlet cavity. As a result, this structure can further reduce the amount of sample residuals.

As a further improvement of the present invention, the feeding hole is connected at an upper part of an end of the high-pressure cavity. Thus, the integrated feeding device can be connected to the upper part of the end of the high-pressure cavity, so as to facilitate sample inlet and gas exhaust.

As a further improvement of the present invention, the integrated feeding device includes a second check valve and a stocker, an inlet of a valve base of the second check valve is directly connected with a bottom part of the stocker, an outlet of a valve body of the second check valve is connected with the feeding hole, and the valve body of the second check valve and the stocker compose an integrated structure. Thus, the structure of the ultrahigh-pressure homogenizing integrated device is more compact, so as to facilitate miniaturization design, reduce loss of the materials during disruption, and facilitate operation.

As a further improvement of the present invention, axial lines of the first check valve, the second check valve and the high-pressure cylinder homogenizing main body are perpendicularly intersected. This structure is advantageous for inspecting the pressure in the ultrahigh-pressure homogenizing main body by the pressure gauge, and is advantageous for miniaturization design.

As a further improvement of the present invention, a valve spool and a valve base of the first check valve are in planar contact and sealed, and a valve spool and a valve base of the second check valve are also in planar contact and sealed. This structure is convenient for manufacturing, and an operation stability of the first check valve and the second check valve is improved, and lifetime is extended.

As a further improvement of the present invention, a cup lid is disposed on the stocker, a quick pipe coupler for rapid cleaning is disposed on the cup lid. Thus, contamination of materials can be avoided, and it is convenient for cleaning operation.

As a further improvement of the present invention, a main viewing window for adjustment is disposed at an upper part of the main connecting sleeve, a water circulation window is disposed at a lower part of the main connecting sleeve, an auxiliary viewing window for adjustment is disposed at an upper part of the auxiliary connecting sleeve, an auxiliary water circulation window is disposed at a lower part of the auxiliary connecting sleeve. Thus, it is convenient for viewing and it is convenient for viewing and adjusting and circulating of cooling water.

According to the afore-mentioned second subject, a cell disruptor is provided by the present invention. The cell disruptor includes a casing, wherein a circulated water bath tank and an accommodating cavity are disposed in the casing, an ultrahigh-pressure homogenizing integrated device is disposed in the circulated water bath tank, the ultrahigh-pressure homogenizing integrated device is composed by a long oil cylinder, a main connecting sleeve, a high-pressure cylinder homogenizing main body, an auxiliary connecting sleeve and a short oil cylinder, which are sequentially and coaxially arranged. A linear hydraulic unit composed by an oil tank, a hydraulic manifold block, an oil pump and an electric machinery, which are sequentially and coaxially connected, is arranged in the accommodating cavity, and an axial line of the linear hydraulic unit is parallel to an axial line of the ultrahigh-pressure homogenizing integrated device.

The axial line of the linear hydraulic unit is parallel to the axial line of the ultrahigh-pressure homogenizing integrated device, so that the cell disruptor has a compact whole structure, reduced volume and occupied space, fewer connection pipes and joints, such that the cell disruptor is unsusceptible to leakage. The ultrahigh-pressure homogenizing integrated device can be immersed in a circulated water bath by applying the circulated water bath tank, so as to avoid from temperature increase, and keep consistent temperature, in order to ensure long operation time of the equipment. The ultrahigh-pressure homogenizing integrated device is driven by hydraulic pressure, so that it can be readily turned off, turned on and paused under a state of high pressure, which would not lead to pressure change, and would not lead to failure while operating without loading.

As a further improvement of the present invention, a feeding hole communicated with a high-pressure cavity and connected with an integrated feeding device is disposed at an upper part of the high-pressure cylinder homogenizing main body, a pressure gauge connection port is disposed at a left side of the high-pressure cylinder homogenizing main body and communicated with the high-pressure cavity, a first check valve is disposed in the pressure gauge connection port, a liquid outlet is located at a right side of the high-pressure cylinder homogenizing main body, the liquid outlet is communicated with a bottom part of a sample outlet cavity in the high-pressure cylinder homogenizing main body, and an angle between an axial line of the liquid outlet and a horizontal direction is 20°. As a result, the ultrahigh-pressure homogenizing integrated device has a compact structure, reduced volume of the whole structure, great operation stability, and improved disruption efficiency. Comparing to a manner of disposing a liquid outlet at an upper part of the high-pressure cylinder homogenizing main body in the prior art, the liquid outlet is disposed at the right side of the high-pressure cylinder homogenizing main body and inclined at an angle of 20° to the horizontal direction in the present invention, a length of an outlet pipe connected to the liquid outlet can be reduced, and the occupied space can be reduced. In addition, a resistance of liquid discharging is reduced, so that liquid discharging can be more fluent, that is unsusceptible to leave residuals, and it is very convenient to arrange the liquid outlet pipe at the liquid outlet.

As a further improvement of the present invention, the sample outlet cavity is in a ring shape, the liquid outlet is tangent to a circumference of the bottom part of the sample outlet cavity. This structure can further reduce the amount of sample residuals.

As a further improvement of the present invention, the feeding hole is connected at an upper part of an end of the high-pressure cavity. As a result, it is advantageous for sample inlet and gas exhaust.

As a further improvement of the present invention, a portion of a valve body of the first check valve is located in the high-pressure cylinder homogenizing main body, and composes an integrated structure with the high-pressure cylinder homogenizing main body. As a result, the structure of the ultrahigh-pressure homogenizing main body is more compact, so as to reduce the volume of the whole structure, and can prevent from pulsations of a high-pressure gauge that avoids the high-pressure gauge from damaging.

As a further improvement of the present invention, the integrated feeding device includes a second check valve and a stocker, an inlet of a valve base of the second check valve is directly connected with a bottom part of the stocker, an outlet of a valve body of the second check valve is connected with the feeding hole, and the valve body of the second check valve and the stocker compose an integrated structure, axial lines of the first check valve, the second check valve and the high-pressure cylinder homogenizing body are perpendicularly intersected. As a result, the structure of the ultrahigh-pressure homogenizing integrated device is more compact, so as to reduce the volume of the whole structure, that is advantageous for miniaturization design. In addition, loss of the sample materials during disruption can be reduced, and it is convenient for operation. Furthermore, it is advantageous for accurately inspecting the pressure in the ultrahigh-pressure homogenizing integrated device by the pressure gauge.

As a further improvement of the present invention, further including a pressure regulating valve, a pressure relief valve and a pressure gauge, wherein the pressure regulating valve and the pressure relief valve are located in the accommodating cavity and fixed on the casing, the short oil cylinder is connected to the pressure regulating valve via a pipe, the pressure regulating valve is connected to the hydraulic manifold block via a pipe, the pressure gauge is arranged at a top part of the casing, the pressure gauge is connected to the pressure relief valve via a pipe, and the pressure relief valve is connected to the first check valve via a pipe. The pressure of the short oil cylinder can be adjusted by applying the pressure regulating valve, so as to adjust disruption pressure, and improve disruption efficiency. The pressure gauge can be protected by applying the pressure relief valve, in order to avoid the pressure gauge from damaging, and to extend its lifetime. The pressure regulating valve and the pressure relief valve are disposed in the accommodating cavity, so that an external space of the cell disruptor would not be occupied, thus it is advantageous for miniaturization design.

As a further improvement of the present invention, a main viewing window for adjustment is disposed at an upper part of the main connecting sleeve, a water circulation window is disposed at a lower part of the main connecting sleeve, an auxiliary viewing window for adjustment is disposed at an upper part of the auxiliary connecting sleeve, an auxiliary water circulation window is disposed at a lower part of the auxiliary connecting sleeve. Thus, it is convenient for viewing and adjusting and circulating of cooling water.

As a further improvement of the present invention, the accommodating cavity is located at a side of the circulated water bath tank or below the circulated water bath tank. This structure can facilitate miniaturization design of the cell disruptor.

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
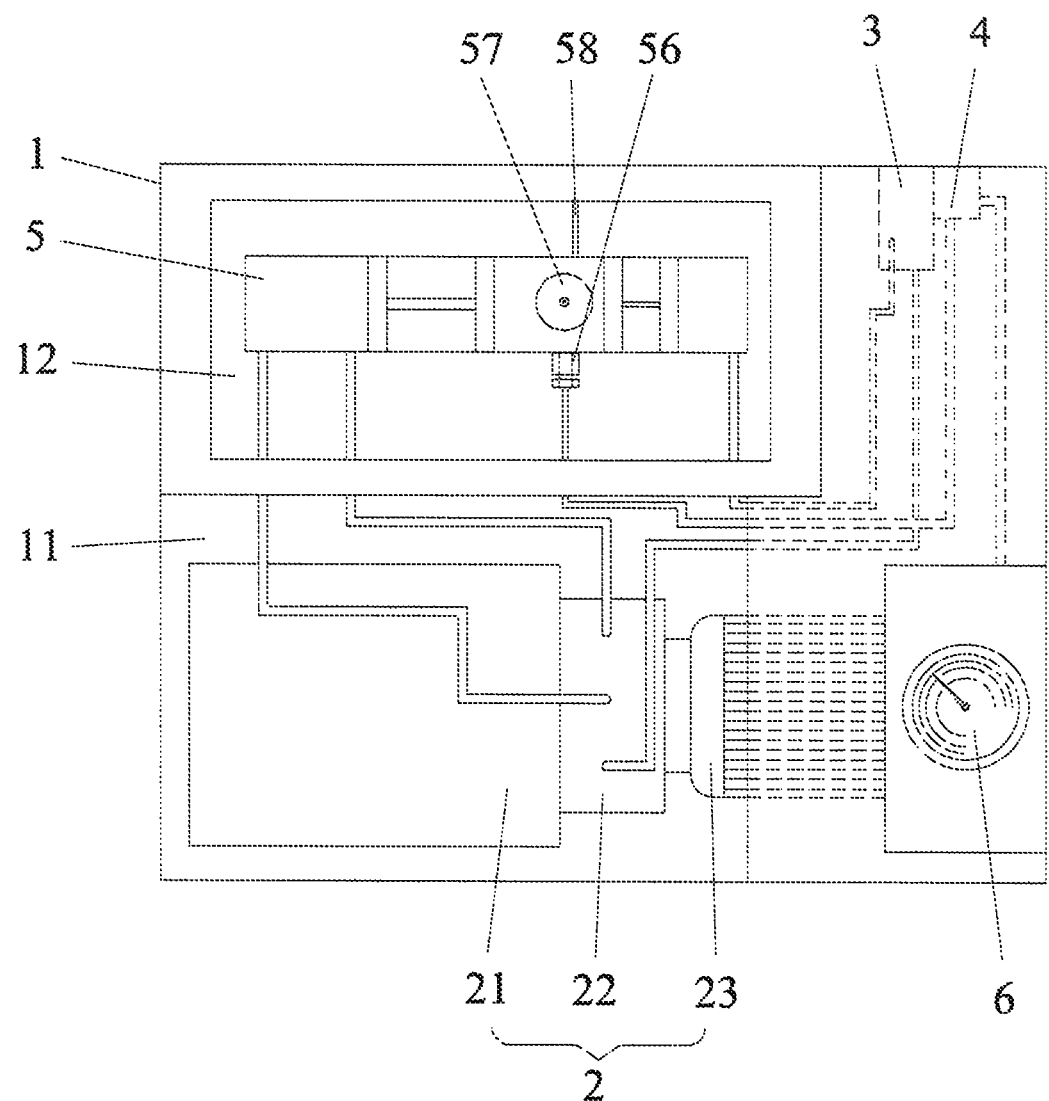
FIG. 1 is a top view of a cell disruptor of the present invention.

Reference will now be made in detail to the present preferred embodiments of the invention, examples of which are illustrated in the accompanying drawings. Wherever possible, the same reference numbers are used in the drawings and the description to refer to the same or like parts.

Figure 2:
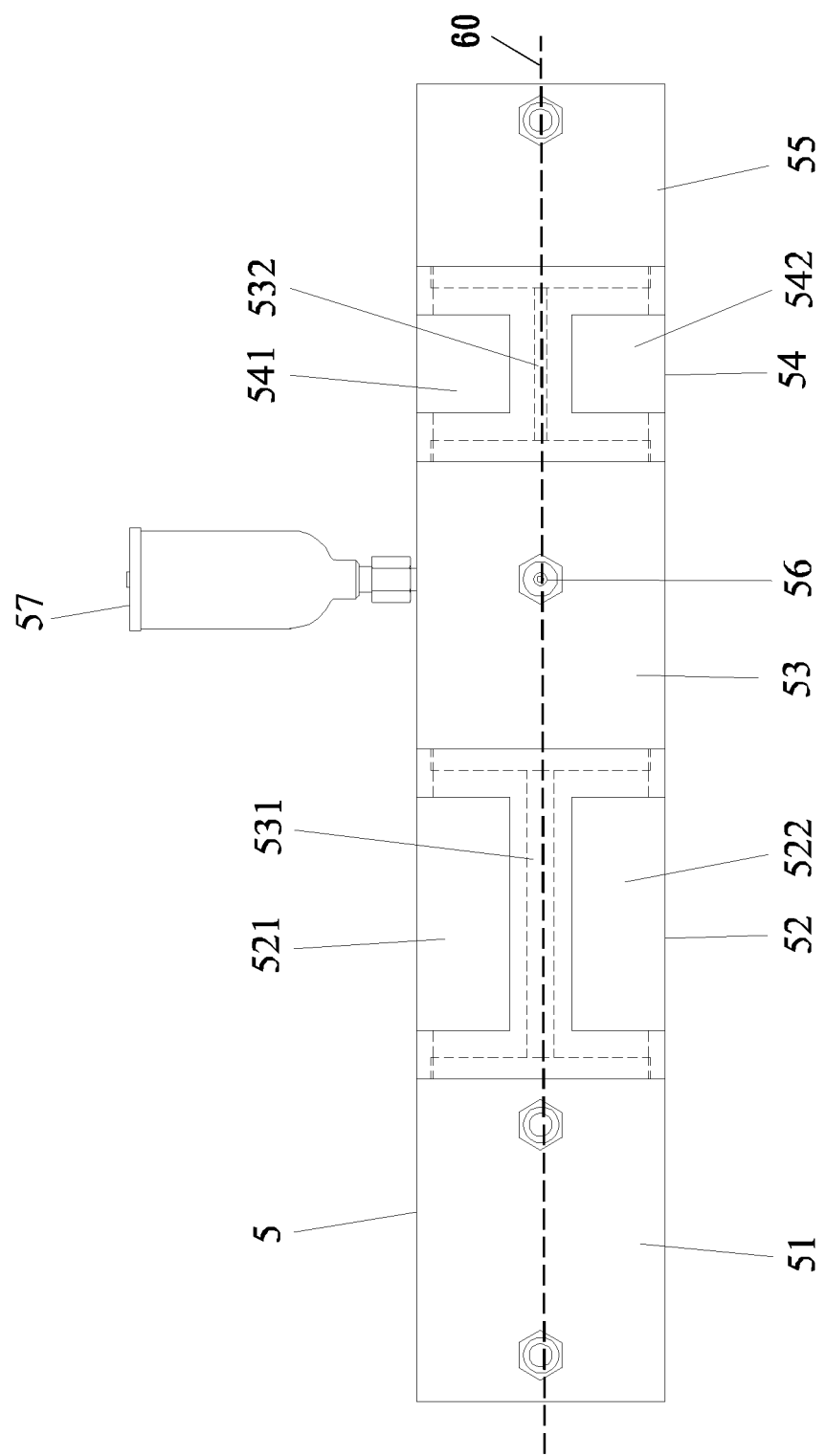
FIG. 2 is a front view of an ultrahigh-pressure homogenizing integrated device.
Figure 3:
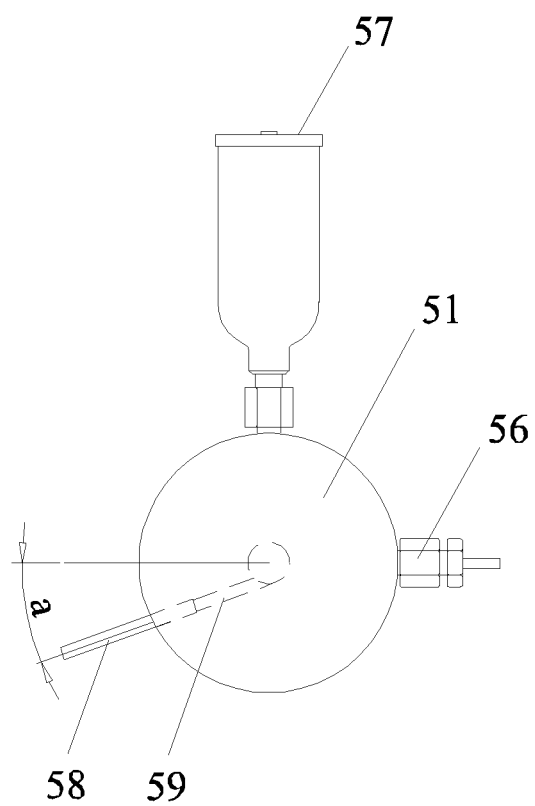
FIG. 3 is a left side view of the ultrahigh-pressure homogenizing integrated device.
Figure 4:
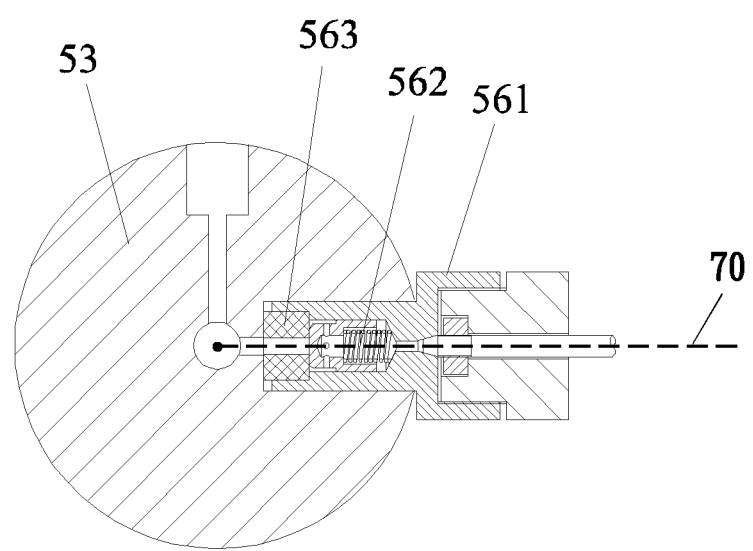
FIG. 4 is a cross-sectional view of a high-pressure cylinder homogenizing main body.
Figure 5:
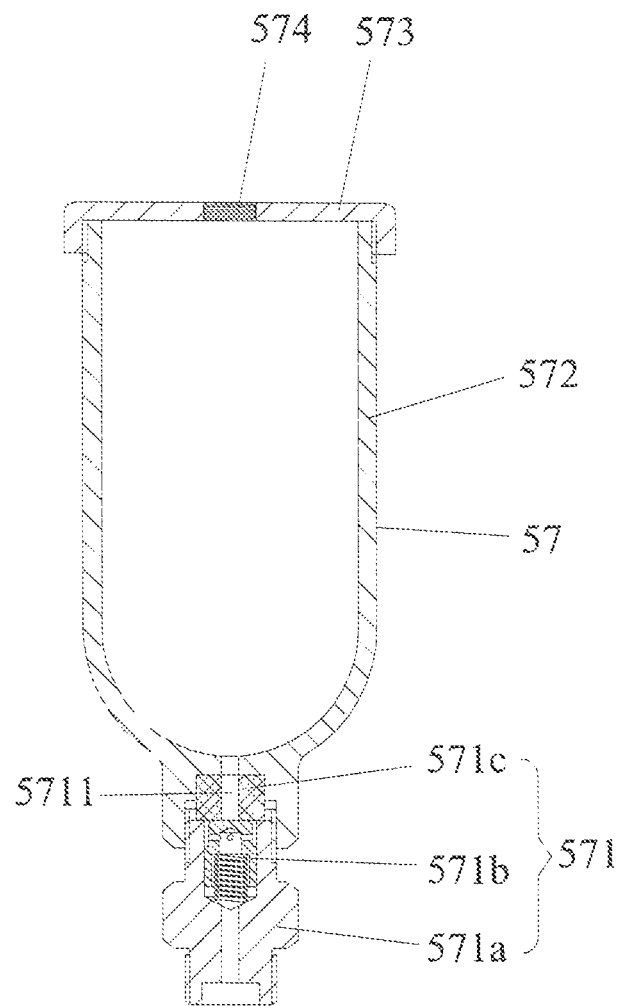
FIG. 5 is a cross-sectional view of an integrated feeding device.

Please refer to FIG. 1 through FIG. 5, a cell disruptor of the present invention includes a casing 1. An accommodating cavity 11 and a circulated water bath tank 12 are disposed in the casing 1, and the accommodating cavity 11 is located at a side of the circulated water bath tank 12. In other embodiments, the accommodating cavity 11 may be disposed below the circulated water bath tank 12 as well, as long as satisfying a miniaturization design of the cell disruptor. A linear hydraulic unit 2, a pressure regulating valve 3 and a pressure relief valve 4 are arranged in the accommodating cavity 11. An ultrahigh-pressure homogenizing integrated device 5 is arranged in the circulated water bath tank 12. The pressure regulating valve 3 and the pressure relief valve 4 are both fixed on the casing 1, and the pressure regulating valve 3 is connected to the hydraulic unit 2 via a pipe. A pressure gauge 6 is arranged at a top part of the casing 1, and the pressure gauge 6 is connected to the pressure relief valve 4 via a pipe.

To be more specific, the accommodating cavity 11 is composed by a first portion parallel to the circulated water bath tank 12 and a second portion perpendicular to the first portion. The second portion is located at an end of the circulated water bath tank 12, the linear hydraulic unit 2 is arranged in the first portion, and the pressure regulating valve 3 and the pressure relief valve 4 are arranged in the second portion.

The linear hydraulic unit 2 is composed by an oil tank 21, a hydraulic manifold block 22, an oil pump and an electric machinery 23, which are sequentially and coaxially connected. The pressure regulating valve 3 is connected to the hydraulic manifold block 22 via a pipe.

The ultrahigh-pressure homogenizing integrated device 5 includes a long oil cylinder 51, a main connecting sleeve 52, a high-pressure cylinder homogenizing main body 53, an auxiliary connecting sleeve 54 and a short oil cylinder 55, which are coaxially and sequentially arranged from left to right. An axial line of the linear hydraulic unit is parallel to an axial line 60 of the ultrahigh-pressure homogenizing integrated device 5. Thus, a whole structure of the cell disruptor is compact, and a volume and an occupied space are reduced. Moreover, the number of connecting pipes and joints is reduced, so as to prevent leakage. A screw thread at a left side of the high-pressure cylinder homogenizing main body 53 and a screw thread at a side of the long oil cylinder 51 are connected via screw threads at both sides of the main connecting sleeve 52 to compose an integrated structure. A screw thread at a right side of the high-pressure cylinder homogenizing main body 53 and a screw thread at a side of the short oil cylinder 55 are connected via screw threads at both sides of the auxiliary connecting sleeve 54 to compose an integrated structure.

A main viewing window for adjustment 521 is disposed at an upper part of the main connecting sleeve 52, and a water circulation window 522 is disposed at a lower part of the main connecting sleeve 52. An auxiliary viewing window for adjustment 541 is disposed at an upper part of the auxiliary connecting sleeve 54, and an auxiliary water circulation window 542 is disposed at a lower part of the auxiliary connecting sleeve 54. The main viewing window for adjustment 521 and the auxiliary viewing window for adjustment 541 can facilitate viewing and adjusting, and the water circulation window 522 and the auxiliary water circulation window 542 can facilitate circulation of cooling water. The long oil cylinder 51 is connected with the hydraulic manifold block 22 of the hydraulic unit 2 via a pipe, the short oil cylinder 55 is connected to the pressure regulating valve 3 via a pipe, and the pressure regulating valve 3 is further connected to the hydraulic manifold block 22 of the hydraulic unit 2. Thus, the short oil cylinder 55 is connected with the hydraulic manifold block 22 of the hydraulic unit 2.

Furthermore, a pressurizing plunger rod 531 capable of moving back and forth is disposed in the high-pressure cavity of the high-pressure cylinder homogenizing main body 53, and the pressurizing plunger rod 531 is protruded from a left side of the high-pressure cylinder homogenizing main body 53 and connected with a piston rod of the long oil cylinder 51. The long oil cylinder 51 is a main oil cylinder which causes the pressurizing plunger rod 531 move. A homogenizing valve communicated with the high-pressure cavity is disposed in an inner cavity of the high-pressure cylinder homogenizing main body 53, a liquid inlet of the homogenizing valve is communicated with the inner cavity of the high-pressure cylinder homogenizing main body 53, and the liquid inlet and the inner cavity are located at a same axial line. Therefore, pressurization and homogenization of materials can be completed in a very short distance, and connecting additional external pipes are not necessary, so as to facilitate assembly and usage, while a volume of the whole structure is reduced, which is advantageous for miniaturization design. The homogenizing valve is connected with an ejector rod 532 of the short oil cylinder 55, and the short oil cylinder 55 is an auxiliary oil cylinder used to control disruption pressure. A dual directional oil cylinder (i.e. applying the long oil cylinder 51 and the short oil cylinder 55 at both sides of the high-pressure cylinder homogenizing main body 53) can greatly simplify a conventional whole structure, reduce the number of connectors and check valves, so as to reduce a failure rate, and facilitate inspection and parts repair/renewal.

A pressure gauge connection port communicated with the high-pressure cavity is disposed at a left side of the high-pressure cylinder homogenizing main body 53, a first check valve 56 is disposed in the pressure gauge connection port, and the first check valve 56 is connected to the pressure relief valve 4 via a pipe. A feeding hole communicated with the high-pressure cavity is disposed at an upper part of the high-pressure cylinder homogenizing main body 53, the feeding hole is connected with an upper part of an end of the high-pressure cavity, and an integrated feeding device 57 is connected with the feeding hole. Accordingly, the integrated feeding device 57 is connected at the upper part of the end of the high-pressure cavity to facilitate sample injection and gas exhaust. A liquid outlet 59 connected with a liquid outlet pipe 58 is further disposed at the high-pressure cylinder homogenizing main body 53, the liquid outlet 59 is located at a right side of the high-pressure cylinder homogenizing body 53, and the liquid outlet 59 is communicated with a bottom part of a sample outlet cavity in the high-pressure cylinder homogenizing main body 53. In addition, an angle between an axial line of the liquid outlet 59 and a horizontal direction is 20°. Thus, resistance of liquid discharging is lowered, fluency of liquid discharging is improved, residuals are not readily formed, and it is advantageous for assembling the liquid outlet pipe 58. Moreover, the sample outlet cavity is in a ring shape, the liquid outlet 59 is tangent to a bottom part of the sample outlet cavity, so as to further reduce an amount of sample residuals.

Furthermore, the first check valve 56 includes a first valve body 561, a first valve spool 562 and a first valve base 563. The first valve spool 562 and the first valve base 563 are located in a channel of the first valve body 561, and the first valve spool 562 and the first valve base 563 are in planar contact and sealed. Thus, operation stability is improved, and lifetime is extended. A portion of the first valve body 561 is located in the high-pressure cylinder homogenizing main body 53, and composes an integrated structure with the high-pressure cylinder homogenizing main body 53. Another portion of the first valve body 561 is located outside of the high-pressure cylinder homogenizing main body 53, so as to improve stability of the ultrahigh-pressure homogenizing integrated device, and prevent from damaging the high-pressure gauge due to pulsation. In addition, the ultrahigh-pressure homogenizing integrated device has a compact structure, which is advantageous for reducing volume of the whole structure.

The integrated feeding device 57 includes a second check valve 571 and a stocker 572, an axial line 70 of the first check valve 56, an axial line of the second check valve 571 and the axial line 60 of the high-pressure cylinder homogenizing main body 53 are perpendicularly intersected, which further facilitates the pressure gauge inspecting the pressure in the pressurized homogenizing integrated device precisely, and is advantageous for miniaturization design. The second check valve 571 includes a second valve body 571a, a second valve spool 571b and a second valve base 571c. The second valve spool 571b and the second valve base 571c are located in a channel of the second valve body 571a, and the second valve spool 571b and the second valve base 571c are in planar contact and sealed. Thus, operation stability is improved, and lifetime is extended. The second valve body 571a and the stocker 572 compose an integrated structure. An inlet 5711 is disposed in the second valve base 571c, the inlet 5711 is directly connected with a bottom part of the stocker 572, and an outlet of the second valve body 571a of the second check valve 571 is connected with the feeding hole. Therefore, long connection pipes are not necessary, and loss of sample materials can be greatly reduced. A minimum amount of the sample to be disrupted is merely 3 ml to 5 ml each time. In addition, a stainless steel needle can be inserted into the stocker 572 to exhaust gas during gas exhaust of the second check valve 571, which is convenient and easy for operation. A cup lid 573 is disposed on the stocker 572. The cup lid 573 and the stocker 572 are connected by a sleeve or a screw thread, to facilitate adding samples and taking off the cup lid 573 during gas exhaust from the inside of the second check valve 571. A quick pipe coupler 574 is disposed on the cup lid 573 for rapid cleaning, in order to facilitate performing a cleaning operation on the stocker 572.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A cell disruptor, comprising a casing, wherein a circulated water bath tank and an accommodating cavity are disposed in the casing, an ultrahigh-pressure homogenizing integrated device is disposed in the circulated water bath tank, the ultrahigh-pressure homogenizing integrated device is composed by a long oil cylinder, a main connecting sleeve, a high-pressure cylinder homogenizing main body, an auxiliary connecting sleeve and a short oil cylinder, which are sequentially and coaxially arranged, wherein a pressure gauge connection port is disposed at a left side of the high-pressure cylinder homogenizing main body and communicated with a high-pressure cavity, wherein a first check valve is disposed in the pressure gauge connection port, wherein a liquid outlet is located at a right side of the high-pressure cylinder homogenizing main body, the liquid outlet is communicated with a bottom part of a sample outlet cavity in the high-pressure cylinder homogenizing main body, and an angle between an axial line of the liquid outlet and a first plane is 20°, and wherein the first plane is formed by an axial line of the first check valve and an axial line of the high-pressure cylinder homogenizing main body perpendicularly intersected with the axial line of the first check valve.

2. The cell disruptor according to claim 1, wherein a linear hydraulic unit composed by an oil tank, a hydraulic manifold block, an oil pump and an electric machinery, which are sequentially and coaxially connected, is arranged in the accommodating cavity, and an axial line of the linear hydraulic unit is parallel to an axial line of the ultrahigh-pressure homogenizing integrated device.

3. The cell disruptor according to claim 1, wherein a feeding hole communicated with the high-pressure cavity and connected with an integrated feeding device is disposed at an upper part of the high-pressure cylinder homogenizing main body.

4. The cell disruptor according to claim 3, wherein the feeding hole is connected at an upper part of an end of the high-pressure cavity.

5. The cell disruptor according to claim 3, wherein the sample outlet cavity is in a ring shape.

6. The cell disruptor according to claim 5, wherein a portion of a valve body of the first check valve is located in the high-pressure cylinder homogenizing main body, and composes an integrated structure with the high-pressure cylinder homogenizing main body.

7. The cell disruptor according to claim 6, wherein the integrated feeding device comprises a second check valve and a stocker, an inlet of a valve base of the second check valve is directly connected with a bottom part of the stocker, an outlet of a valve body of the second check valve is connected with the feeding hole, and the valve body of the second check valve and the stocker compose an integrated structure, axial lines of the first check valve, the second check valve and the high-pressure cylinder homogenizing body are perpendicularly intersected.

8. The cell disruptor according to claim 7, further comprising a pressure regulating valve, a pressure relief valve and a pressure gauge, wherein the pressure regulating valve and the pressure relief valve are located in the accommodating cavity and fixed on the casing, the short oil cylinder is connected to the pressure regulating valve via a pipe, the pressure regulating valve is connected to a hydraulic manifold block via a pipe, the pressure gauge is connected to the pressure relief valve via a pipe, and the pressure relief valve is connected to the first check valve via a pipe.

9. The cell disruptor according to claim 1, wherein a main viewing window for adjustment is disposed at an upper part of the main connecting sleeve, a water circulation window is disposed at a lower part of the main connecting sleeve, an auxiliary viewing window for adjustment is disposed at an upper part of the auxiliary connecting sleeve, and an auxiliary water circulation window is disposed at a lower part of the auxiliary connecting sleeve.

10. The cell disruptor according to claim 1, wherein the accommodating cavity is located at a side of the circulated water bath tank or below the circulated water bath tank.

\* \* \* \* \*